United States Patent [19]

Bosselman et al.

[11] Patent Number: 5,162,215
[45] Date of Patent: Nov. 10, 1992

[54] METHOD OF GENE TRANSFER INTO CHICKENS AND OTHER AVIAN SPECIES

[75] Inventors: Robert A. Bosselman, Thousand Oaks; Shaw-Fen S. Hu, Newbury Park; Margery A. Nicolson, Pacific Palisades, all of Calif.

[73] Assignees: Amgen Inc., Thousand Oaks, Calif.; Arbor Acres Farm, Inc., Glastonbury, Conn.

[21] Appl. No.: 247,964

[22] Filed: Sep. 22, 1988

[51] Int. Cl.$^5$ .............................................. C12N 15/00
[52] U.S. Cl. .............................. 435/172.3; 435/320.1; 435/948; 800/2; 800/DIG. 1; 935/57; 935/111
[58] Field of Search .............................. 800/2, DIG. 1; 435/172.3, 317.1, 320.1, 948; 935/32, 57, 70, 111

[56] References Cited

PUBLICATIONS

Shuman et al. (a), Poultry Science 67 (Suppl.): 34 (1988).
Shuman et al. (b), Poultry Science 65:1437–1444 (1986).
Salter et al., Virology 157: 236–240 (1987).
Emerman et al., Cell 39: 459–467 (1984).

*Primary Examiner*—Elizabeth C. Weimar
*Assistant Examiner*—Jasemine C. Chambers
*Attorney, Agent, or Firm*—Julia E. Ambers

[57] ABSTRACT

A method for introducing a replication-defective retroviral vector into pluripotent stem cells of embryos of an avian species, including chickens, turkeys, quails or ducks. The method is useful for transferring nucleic acid sequences into embryonic avian cells which may differentiate into somatic or germ cells. Transfer into germ cells has been achieved to produce transgenic animals. The replication-defective retroviral vector used for transfer may be a recombinant retroviral vector containing both a retroviral derived nucleic acid sequence and a non-retroviral derived nucleic acid sequence. Examples of non-retroviral nucleic acid sequences are a neomycin resistance gene from the bacterial transposon Tn5, a herpes simplex virus thymidine kinase gene and a chicken growth hormone gene, however, any prokaryotic or eukaryotic nucleic acid sequence of interest may be used. Transgenic chickens have been produced whose cells contain and express a replication-defective retroviral vector nucleic acid sequence.

12 Claims, 3 Drawing Sheets

METHOD OF GENE TRANSFER INTO CHICKENS AND OTHER AVIAN SPECIES

BACKGROUND OF THE INVENTION

A. Field of the Invention

The present invention encompasses a method for introducing foreign genetic material into somatic and germ cells of the chicken and other avian species. The invention further encompasses a method for introducing foreign genetic material into a chicken embryo resulting in the production of a transgenic chicken.

B. Description of the Art

There has been much interest in introducing foreign DNA into eukaryotic cells. One reason for this interest is that some genetically caused diseases may be curable by introducing the foreign DNA into the cells, allowing the foreign DNA to express a protein that the genetically defective cell cannot express. Another reason for this interest is that certain eukaryotic cells may prove to be the most suitable hosts for the production of certain eukaryotic proteins. The feasibility of introducing foreign DNA into animal genomes and thus being able to alter the phenotype of an intact animal by the insertion of this foreign DNA has stimulated considerable interest in the development of methods for gene transfer.

Successful methods of transfer of foreign genes into the germ cells of chickens would permit basic studies of gene expression in the avian system, and ultimately would permit the introduction of genes that may be used for poultry improvement. Gene transfer into chickens could thus potentially affect the long-range improvement of poultry by giving the breeder a new tool—a molecular genetic approach to breeding problems. Several advantages of such an approach are that: (a) gene transfer provides a means of increasing genetic variation by the introduction of genetic material into the genome, which permits gene flow between vastly different organisms and which transcends the limits of sexual reproduction; (b) gene transfer permits the formation of new phenotypes which may have increased economic value; and (c) gene insertion may permit the transfer of favorable traits between various stocks of chickens without concomitant transfer of less favorable genes that occurs using current methods of backcrossing.

The ability to manipulate the mouse embryo has led to a variety of successful approaches to gene transfer in this species. These include microinjection of DNA (Palmiter and Brinster, Cell 41:343-345 (1985) retroviral infection of young embryos (Jaenisch, Proc. Natl. Acad. Sci. USA 73:1260-1264 (1976); Soriano et al., Science 234:1409-1413 (1986)), and genetic modification of cultured pluripotential embryonic stem cells which can contribute to the germ-cell lineage of chimeric mice. Bradley et al., Nature 309:255-256 (1984); Robertson et al., Nature 323:445-448 (1986). In particular, the production of transgenic mice is now routinely achieved by microinjection of foreign DNA into male pronuclei of fertilized eggs. Palmiter et al., Nature 300:611-15 (1982). Microinjected eggs are then implanted into the oviducts of one-day pseudopregnant foster mothers and carried to term. The newborn mice are then tested for the presence of the microinjected DNA by means known in the art and appropriate to detect the presence of the microinjected DNA. A manual of procedures for microinjection of foreign DNA into isolated mouse egg cells has been published. Hogan et al., *Manipulating the Mouse Embryo*, Cold Spring Harbor Laboratory (1986). More recently, similar microinjection methods have been successfully employed using rabbit, sheep and pig egg cells. Hammer et al., Nature 315:680-683 (1985).

In contrast, similar egg cell microinjection methods for gene transfer have not been successfully applied to chickens because of difficulties involved in manipulating the chicken embryo. When oviposition occurs, the embryo has already reached a stage corresponding to a mammalian late blastula or early gastrula, (Kochav et al., Dev. Biol. 79:296-308 (1980); Eyal-Giladi and Kochav, Develop. Biol. 49:321-337 (1976). Genetic manipulation of the embryo during earlier development requires reintroduction to the female or in vitro culture. Rowlett and Simkiss, Br. Poult. Sci. 28:91-101 (1987); Perry, Nature 331:70-72 (1987). Both are difficult procedures, whose efficiency may limit their application as a method of gene transfer.

Because morphological and developmental characteristics of the early chicken embryo and other avian embryos restrict the use of the microinjection methods of gene transfer that have been used so successfully in the mouse and other species, an alternative method for introducing genes into chicken embryos has been used which involves the infection of embryos with infectious retroviral vectors. Transfer of additional growth hormone genes into chicken somatic cells via a replication competent Rous sarcoma virus (RSV) vector (Souza et al., J. Exp. Zool. 232: 465-473), transfer of replication competent reticuloendotheliosis virus (REV) by injection of virus into developing ovarian follicles near ovulation (Shuman and Shoffner, Poult. Sci. 65: 1437-44 (1986)). and more recently, transfer of RSV derivatives into chicken germ cells (Salter et al., Poult. Sci. 65: 1445-1458 (1986); Salter et al., Virology 157: 236-240 (1987); Salter and Crittenden, Poult. Sci. 66: 170 (1987)) has been accomplished by infection of day-old chicken embryos with replication competent retroviral vectors. Sorge and Hughes, J. Mol. Appl. Genet. 1: 547-559 (1982); Hughes et al., Poult. Sci. 65: 1459-1467 (1986). This approach to avian gene transfer has advantages over DNA microinjection since the early chicken zygote is difficult to manipulate, and even a freshly laid egg contains thousands of cells (Eyal-Giladi and Kochav, supra; Kochav et al., supra). However, the use of replication competent vectors in gene transfer has significant disadvantages. Replication competent vectors result in gene transfer to susceptible cells at various stages of differentiation long after initial infection of the embryo, because they are capable of subsequent rounds of infection after introduction. This can make it difficult to determine the stage of development at which gene insertion takes place, or the cell lineage relationship within fully differentiated tissues. Furthermore, replication competent vectors also increase the potential for disease states associated with chronic viral infection. Salter, et al., Poult. Sci. 65:1445-1458 (1986). More importantly, it is unacceptable to introduce infectious replication competent retroviral vectors into the germ cells of poultry intended for commercial use. Therefore, there was a need for the development of efficient vectors and efficient procedures using such vectors that would permit insertion of a foreign gene into cells in an initial round of infection but wherein the vectors would not permit reinfection of the cells after the initial round of infection. Several replication-defective retroviral vector systems have been derived (Bosselman et al., Mol. Cell. Biol. 7:1797-1806 (1987); Cone and Mulligan, Proc. Natl. Acad. Sci. USA 81:6349-6353 (1984); Mann et al., Cell 33:153-159 (1983); Miller and Buttimore, Mol. Cell. Biol. 6:2895-2902 (1986); Watanabe and Temin, Mol. Cell. Biol. 3:2441-249 (1983); Stoker and Bissell, J. Virol. 62:1008-1015 (1988)). One of these systems (Watanabe and Temin, supra) has been derived from the reticuloendotheliosis virus type A (REV-A). Sevoian et al., Avian Dis. 8:336-347 (1964). Replication-defective retroviral vectors derived from the REV-A virus are based on the helper cell line C3 (Watanabe and Temin, supra) which contains a packaging defective helper provirus. The derivation of the C3 helper line and several replication-defective retroviral vectors have been described in detail in U.S. Pat. No. 4,650,764, which is hereby incorporated by reference in its entirety. Several other retroviral vectors have been described by Emerman and Temin, Cell 39:459-467 (1984), which is hereby incorporated by reference in its entirety.

Shuman and Shoffner (Poult. Sci. 65: 1437-44 (1986)) used a replication-defective retroviral vector constructed by Emerman and Temin, supra, containing a bacterial gene for neomycin resistance and a herpes virus thymidine kinase gene, to inject into developing ovarian follicles prior to ovulation. This system involves gene transfer by injection at the single cell (ova) stage before fertilization and cleavage. Of 27 chicks examined two were tentatively identified with DNA sequences that hybridized to radiolabeled vector probes. However, the vector sequences were not completely characterized nor was the presence of replication competent virus ruled out. No progeny from these chickens were available to test whether any vector sequence was passed through the germ cells.

Thus, there is limited success to date in methods of gene transfer in chickens using replication-defective retroviral vectors, in particular, defective REV vectors. To date, there is no report of successful transfer of replication-defective retroviral vector sequences into developing chick embryos without the use of replication competent REV helper virus. The art has not yet been provided with a method of gene transfer into chicken or other avian embryos which permits the stable integration of vector into somatic and/or germ cells of the embryo using a replication-defective retroviral vector without significant helper virus. The problem has been to discover a stage of early avian development at which pluripotent stem cells of the embryo are both susceptible to infection by the replication defective retrovirus and able to be reached with sufficient vector to permit effective delivery to such cells. Thus, it can be seen that a need has existed for a reliable and effective method of transferring a nucleic acid sequence into somatic and germ cells of chicken embryos using a retroviral vector that inserts the nucleic acid sequence in embryonic cells in an initial round of infection but cannot reinfect the cells after the initial round of infection. This is especially critical for introducing genes into chickens or other avian species intended for commercial use.

SUMMARY OF THE INVENTION

A method is described for introducing foreign genes or foreign nucleic acid sequences into somatic and/or germ cells of the chicken and other avian species. A replication-defective retroviral vector is used as the vehicle for transfer. The method permits the insertion of a foreign gene or foreign nucleic acid sequence in embryonic cells in an initial round of infection but the vector cannot reinfect the cells after the initial round of infection. The method permits germline transfer of nucleic acid sequences and involves the discovery of a stage of early avian development in which germline stem cells are susceptible to retroviral infection.

A preferred embodiment of the present invention is a method for introducing a replication-defective retroviral vector into a pluripotent stem cell of an unincubated chick embryo, comprising:

(a) making an opening in an unincubated chicken egg containing an embryo to expose a blastoderm;

(b) microinjecting through the opening a solution containing the replication-defective retroviral vector into an area around and in close proximity to the blastoderm; and (c) sealing the opening after microinjection.

This procedure is preferably carried out as follows: the chicken egg is an unincubated day old egg; the opening in the egg is ~5 mm. in diameter; the microinjection of a solution of vector in a volume of about 5-20 $\mu$l is accomplished with a drawn glass needle ~40-60 $\mu$M outer diameter; and the egg is sealed with membrane from a donor egg and with glue or paraffin.

In another embodiment of the present invention, the replication-defective retroviral vector is a recombinant retroviral vector with a first part that is a retroviral derived nucleic acid sequence and a second part that is a non-retroviral derived nucleic acid sequence. Any prokaryotic or eukaryotic non-retroviral gene or nucleic acid sequence may be used as the second part. In a preferred embodiment, the second part sequence is a herpes simplex thymidine kinase gene, a bacterial neomycin resistance gene and/or a chicken growth hormone gene.

The present invention also encompasses transgenic chickens. The germ cells of these transgenic chickens contain transferred nucleic acid sequences. The present invention encompasses a method for obtaining such transgenic chickens.

The objects of this invention therefore include:

(a) providing a reliable and efficient method of transferring nucleic acid sequences into chicken or other avian embryos with replication-defective retroviral vectors that are incapable of reinfection after the initial round of infection;

(b) providing a method of transferring gene encoding and/or regulatory nucleic acid sequences into chicken or other avian embryos at a stage in embryo development at which pluripotent stem cells are both (i) susceptible to infection by the replication-defective retroviral vector, and (ii) able to be reached with sufficient vector to permit effective delivery to the cells;

(c) providing a transgenic chicken whose germ cells contain a transferred retroviral derived nucleic acid sequence and may contain in addition a non-retroviral derived nucleic acid sequence;

(d) providing a method of producing such a transgenic chicken;

(e) providing a method of transferring nucleic acid sequences into chicken embryos that result in transgenic chickens with desirable phenotypes which result from the transferred sequences; and (f) providing a transgenic chicken whose organs, tissues and/or eggs contain desirable protein products.

These and still other objects and advantages of the present invention will be apparent from the description which follows. In the description, the preferred embodiments of the invention will be described with reference to the accompanying drawings. These embodiments do not represent the full scope of the invention. Rather, the invention may be employed in other embodiments. Reference should therefore be made to the claims to interpret the breadth of the invention.

DESCRIPTION OF THE PREFERRED EMBODIMENTS

Figure 1:
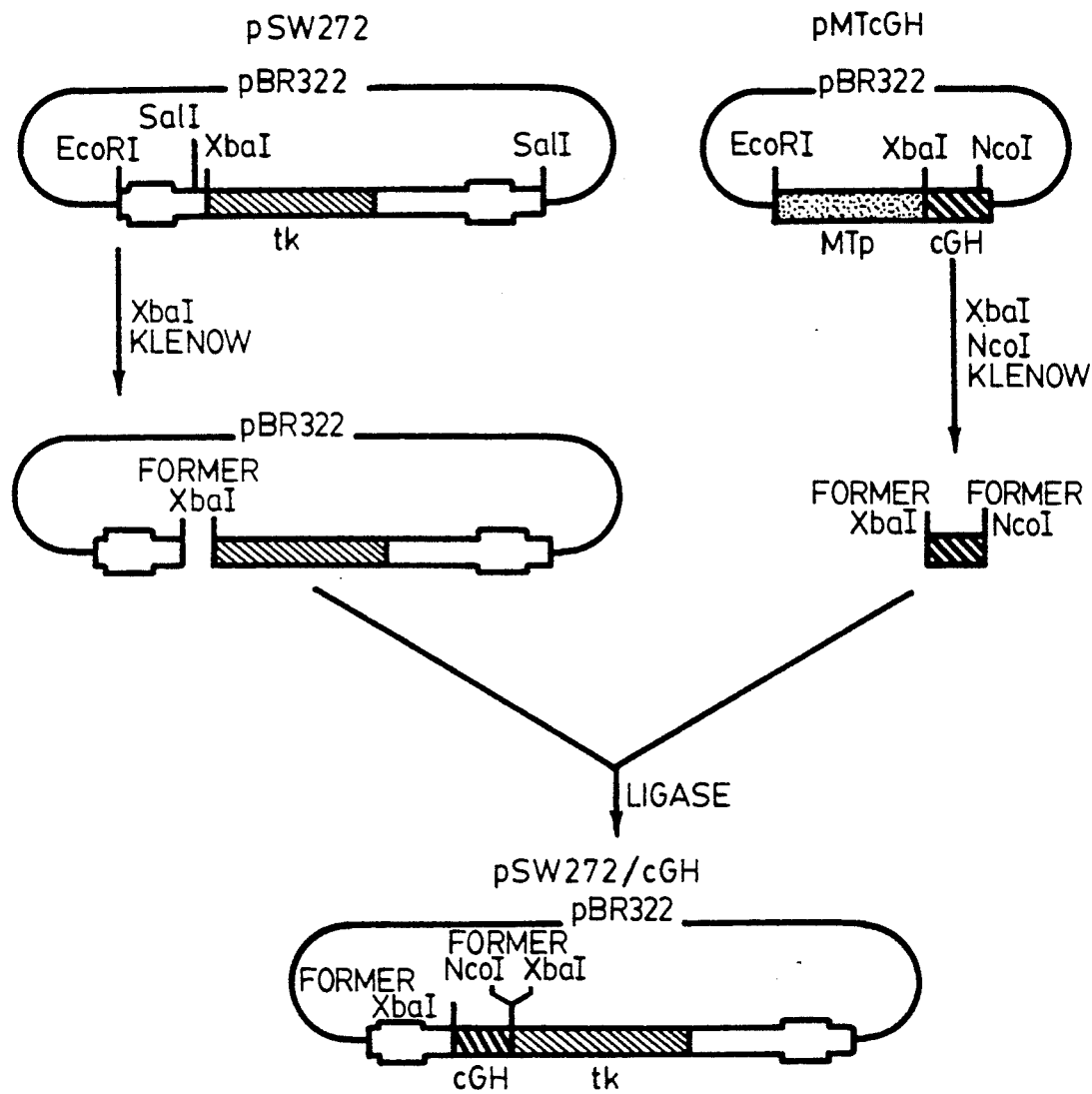
FIG. 1 depicts in schematic form the synthesis of plasmid pSW272/cGH from plasmids pSW272 and pMTcGH.

The ability to transfer nucleic acid sequences into the avian genome represents an important step toward understanding and manipulating the genetic basis of avian physiology. Of particular interest is the ability to transfer nucleic acid sequences, including gene-encoding sequences that may be used for poultry improvement, for example, to produce desirable phenotypes including disease resistance and/or desirable protein products in a variety of avian species, in particular, in chickens. The transferred nucleic acid sequences may include the following: (i) sequences encoding a hormone (for example. Palmiter et al., Nature 300:611–615 (1982)), such as growth hormone or insulin-like growth factor I. wherein such hormones might affect the growth of animals; (ii) sequences encoding a growth hormone releasing factor (for example. Hammer et al., Nature 315:413–416 (1985)), wherein such factor might alter hormone release from the pituitary gland and ultimately affect growth; (iii) sequences encoding an anti-mullerian hormone, (for example, Josso, Endocrine Reviews 7:421–433 (1986); Liu et al., Seminars in Reproductive Endocrinology 5:283-294 (1987); Picard et al., Proc. Natl. Acad. Sci. USA 83:5464–5468 (1986); Rashedi and Maraud, Gen. Comp. Endocrin. 65:87-91 (1987)), wherein the hormone might contribute to phenotypic maleness (i.e., improved growth rates, better feed conversion, lower body fat content) in otherwise genetically female animals; (iv) sequences which act as enhancers of transcription (for example, Linney et al., Nature 308:470-472; Laimins et al., Proc. Natl.Acad.Sci. USA 79:6453-6457 (1982); Levinson et al., Nature 295:568-572 (1982)). including modified tissue specific transcriptional enhancer sequences; (v) sequences containing promoter sequences of cellular or viral origin, but not containing viral LTR promoter sequences (for example, Dougherty and Temin, Proc. Natl. Acad.Sci. USA 84:1197–1201 (1987)); (vi) sequences encoding trans-acting protein factors which regulate the expression of other genes (for example, any of the transcription regulating proteins listed in Wingender, Nucl. Acids Res. 16 1879-1902 (1988)); (vii) sequences containing antisense coding sequences complementary to other gene coding or non-coding sequences (for example, Cell 53:601–615 (1988)), whereby transcription of antisense genes could interfere with the function of other complementary gene sequences; and (viii) sequences encoding aromatase, an enzyme involved in the conversion of the male hormone testosterone to the female hormone estrogen (for example, Wilson et al., Endocrine Reviews 8:363–376 (1987)), wherein the enzyme might cause phenotypic female traits (i e., feathering). In addition, the transferred nucleic acid sequences might encode the following desirable protein products: blood proteins including human serum albumin or $\alpha$1-antitrypsin, blood clotting proteins including factor VIII, hematopoietic growth factors including erythropoietin, and lymphopoietic growth factors including granulocyte colony stimulating factor. The present invention encompasses transgenic chickens whose organs, tissues and/or eggs may contain a desirable protein product, including any of the above listed proteins.

The following discussion, including the examples, covers the derivation and use of REV-derived replication-defective vectors to transfer new genetic information into chicken embryos. There are several techniques currently available for the transfer of exogenous genetic material into animal cells. These techniques include mechanical or chemical methods such as microinjection of DNA, uptake of DNA in the form of calcium-phosphate precipitates, and DNA transfer mediated by liposomes DNA virus vectors or RNA virus vectors provide alternatives to such mechanical or chemical methods. To date, microinjection has been the predominant method for the insertion of genes into the egg cells of certain mammalian systems, although this has not been effective for avian systems. Chemical methods and DNA viruses have been used for gene transfer into cultured cells. RNA viruses or retroviruses, in contrast, are ideally suited as vectors for the introduction of new genetic material (protein-encoding and/or regulatory nucleic acid sequences) into avian genomes Retroviral vectors have (1) an efficient method to gain entry into the host cell and (2) an efficient method of integration into a host cell chromosome. Although replication competent vectors have been used successfully in avian gene transfer, such infectious viral vectors are not suitable for introducing genes into avian species, such as chickens or turkeys, which are intended for commercial use. In contrast, replication-defective retroviral vectors are ideal for avian gene transfer, however, prior to the present invention no one has been able to achieve transfer of nucleic acid sequences into avian germ cells using such replication-defective vectors. In particular, the advantages of using REV-derived replication-defective vectors for germ cell gene transfer into chickens include the following: (1) chickens do not contain endogenous REV which might interfere with detection of newly acquired provirus; and (2) gene transfer by defective retroviral infection circumvents many of the technical problems associated with other methods of avian gene transfer. In vitro REV vectors transduce and express the chicken growth hormone coding sequence, and the Herpes Simplex Virus I thymidine kinase gene. In vivo, REV vectors may efficiently transfer these same genes along with retroviral sequences into chicken embryos, resulting in the production of transgenic chickens. Because of the broad host range of REV in avian species, such vectors may also be used to transfer new genetic information into avian species other than chickens. Witter and Johnson, Avian Dis. 29:1140-1154 (1985). The problem has been to discover a window in development in which chicken or other avian cells, in particular, the pluripotent stem cells, express viral receptor so as to be susceptible to infection. A second problem has been to discover conditions of administering the REV-derived replication-defective vector such that sufficient amounts are delivered to such susceptible stem cells. The method of the present invention has solved both problems by identifying a window in development in which chicken pluripotent stem cells are susceptible to REV infection and providing vector in amounts effective to infect susceptible cells.

The term "chicken growth hormone" refers not only to natural growth hormone, but also to any analogue thereof. Examples of such analogues are: the product of a chicken growth hormone gene which contains a mutation rendering the growth hormone thereby produced to be functionally impaired, or a naturally occurring chicken protein which is structurally or functionally similar to normal chicken growth hormone, or a novel growth hormone which results from the in vitro or in vivo mutagenization or modification of the chicken growth hormone gene. The term "chicken growth hormone" further refers to variant forms of chicken growth hormone. A variant form of chicken growth hormone is a molecule structurally or functionally similar to chicken growth hormone which arises naturally or through disease and is present in a subpopulation of the total population.

The term "non-retroviral sequence" refers to a nucleic acid sequence which is not derived from any retrovirus but may be derived from any prokaryotic or eukaryotic source, including but not limited to bacteria, viruses other than retroviruses, yeast, or any plant, insect, avian, vertebrate, or mammalian source, or a synthetic construct of any such sequence. The term "non-retroviral sequence" further refers to any prokaryotic or eukaryotic nucleic acid sequence that is not derived from any retrovirus including a protein encoding and/or regulatory sequence, and if such a sequence is a protein-encoding sequence that it is capable of being expressed upon the transfer of such a protein-encoding sequence into a chicken embryo. Herpes virus thymidine kinase and chicken growth hormone are examples of non-retroviral protein-encoding sequences which may be expressed in a transgenic chicken.

The term "avian species" includes chicken, quail, turkey, duck and other fowl.

The term "REV-derived replication-defective vector" refers to a reticuloendotheliosis virus vector that is incapable of unrestricted replication (i.e., multiple rounds of infection), usually due to mutations or deletions in the virus genome. Cell lines have been constructed to complement these vectors and produce the viral proteins necessary to package replication-defective retroviral vectors. The packaged vector may infect a cell once, but is incapable itself of subsequent rounds of infection. Examples of such defective vectors illustrated herein include SW272/cGH and ME111.

The term "transgenic chicken" refers to a chicken that contains a transferred nucleic acid sequence, including a transferred protein-encoding and/or regulatory sequence, such that the transferred sequence is integrated into a host chromosome. As a result of such transfer and integration, the transferred sequence may be transmitted through germ cells to the offspring of a transgenic chicken. Thus, transgenic chickens are created by introducing by a method of transfer, new nucleic acid sequences into germ cells.

The term "cloned gene" or "transferred nucleic acid sequence" refers to a DNA sequence of interest, which has been isolated, and is to be microinjected into the chicken embryo, so as to produce a transgenic chicken whose DNA contains the cloned gene sequence.

As used herein, the terms "gene", "DNA sequence", "nucleic acid sequence" or "genetic sequence" are synonymous, and refer to DNA including any introns or exons which are naturally associated with that DNA. An example of a gene is the DNA which encodes chicken growth hormone and the untranslated and intervening sequences which are associated with this DNA sequence. Another example of a gene is the cDNA which encodes chicken growth hormone. One genetic sequence is said to be derived from a second genetic sequence if it is either an exact copy of the second genetic sequence or if it results from an alteration (i.e., mutation, insertion, or deletion) of the second sequence. A genetic sequence may or may not be expressed. A protein-encoding genetic sequence is said to be "expressed" if the gene is transcribed into RNA and the RNA is translated into protein. A regulatory genetic sequence may be expressed if the regulatory sequence is transcribed into RNA. Some regulatory genetic sequences are not expressed.

A cloned gene, or a fragment of a cloned gene to be transferred into a chicken embryo is produced and purified by any of several methods well known to the art. Thus, a cloned gene can be produced synthetically, or by treating mRNA derived from the transcription of the gene with a reverse transcriptase so as to produce a cDNA version of the gene, or by the direct isolation of the gene from a genomic bank or from other sources.

Regardless of how the cloned gene is isolated, it is amplified, and purified away from any other potentially contaminating molecules. Any DNA sequence, such as a chicken growth hormone gene or a thymidine kinase gene or any genetic sequence from a replication-defective retroviral vector may be used, preferably DNA of plasmid pSW272/cGH. which plasmid contains a chicken growth hormone gene, a thymidine kinase gene and genetic sequences of a replication-defective retroviral vector.

Chicken eggs may be prepared for microinjection of a replication-defective REV-derived retroviral vector as follows. An opening about 5 mm. in diameter is made in the side of the egg, normally by the use of a drilling tool fitted with an abrasive rotating tip which can drill a hole in the eggshell without damaging the underlying shell membrane. The membrane is then cut out by use of a scalpel, so that a portion of the shell and membrane is removed thereby exposing the embryo. The embryo is visualized with an optical dissecting microscope with a 6×-50× magnification. A solution, usually tissue culture medium, containing a replication-defective retroviral vector with or without a non-retroviral cloned nucleic acid sequence of interest is microinjected into an area beneath and around the blastoderm, using a micromanipulator and a very small diameter needle, preferably glass, 40–60 μM outer diameter. The volume of solution for microinjection is preferably 5–20 μl. After microinjection, the egg is sealed with shell membrane and a sealing material, preferably glue or paraffin. The sealed egg is then incubated at 37° C. for various time periods up to and including the time of hatching to allow normal embryo growth and development. DNA from embryos and from newly hatched chicks is tested for the presence of sequences from the microinjected vector. Approximately 10-50% of embryos tested contain inserted vector sequences. In addition, approximately 1-8% of the progeny from vector-positive male $G_0$ birds carrying vector sequences in their semen will be transgenic (i e., will contain within the chromosomal DNA of germ cells integrated sequences of the vector).

The presence of these inserted sequences is detected by means known in the art and appropriate to the detection of the specific cloned gene. Thus, to detect a gene which does or does not express a polypeptide product, a Southern blot hybridization analysis is performed. Such techniques, as well as those required for recombinant DNA manipulations, are described in Maniatis, T. et al., *Molecular Cloning: A Laboratory Manual,* Cold Spring Harbor Laboratory, N Y., 1982, hereinafter incorporated Manual. Cold Spring Harbor by reference. Southern blot hybridization analysis can also be used to distinguish an endogenous gene from a gene transferred by microinjection, for example, to distinguish endogenous chicken growth hormone gene from transferred chicken growth hormone gene. Cloned genes, whose presence is expected to be detectable by the production of a polypeptide, such as thymidine kinase, may be detected by means which are capable of distinguishing the product of the cloned gene from any endogenous gene product, such as radioimmunoassay, enzyme assay, or by other means well known in the art. Any suitable means, such as radioimmunoassay, may be used to detect the expression of the cloned gene in the transgenic chicken.

In order to more fully demonstrate the attendant advantages arising from the present invention, the following examples are set forth. It is to be understood that the following is by way of example only and is not intended as an undue limitation on the otherwise broad scope of the invention.

EXAMPLE 1

Construction cGH Transducing Vector

The assembly of a plasmid encoding the chicken growth hormone (cGH) transducing vector SW272/cGH is diagrammed in FIG. 1. The plasmid pMTcGH contains the mouse metallothionein I gene promoter described by Brinster, et al., Nature, 296:39-42 (1982). and contains the cGH gene described by Souza et al., J. Exp Zool. 232:465-473. The parental vector SW272 (U.S Pat. No. 4,650.764; Watanabe and Temin, Molec. Cell. Biol. 2241-2249 (1983)) is derived from spleen necrosis virus (SNV), and contains the herpes thymidine kinase (HSV-I tk) gene and promoter in the same transcriptional orientation as the viral promoter. An XbaI to NcoI fragment containing the cGH coding sequence and pSW272 linearized with XbaI were treated with the Klenow fragment of DNA polymerase I and then ligated. The open portions of the plasmids shown represent viral sequences. Lightly slashed regions correspond to the HSV-I tk gene (tk); heavily slashed regions correspond to cGH coding sequences; the stippled region in pMTcGH corresponds to the EcoRI to BglII fragment of mouse DNA containing the mouse metallothionein I promoter (MTp). Assembly was carried out in derivatives of pBR322 indicated as a single line in FIG. 1.

The cGH coding sequence was originally derived from a cDNA clone made from chicken pituitary messenger RNA Souza, et al., supra. The DNA fragment XbaI to NcoI contains the complete coding sequence of the cGH gene, but lacks the polyA addition signal present at the 3' end of the cDNA. Using Klenow reagent and blunt end ligation, the cGH sequences were inserted into the unique XbaI site within pSW272 located just downstream of the viral 5' splice donor and packaging sequence, 555 nucleotides from the 5' end of the viral RNA transcript. Hu, et al., Virology 159:446-449 (1987); Watanabe and Temin, Proc. Natl. Acad. Sci. USA 79: 5986-5990 (1982). The orientation of the cGH coding sequence is the same as that of the viral sequences. Proceeding from the 5' end of the proviral RNA transcript of SW272/cGH, the first ATG encountered codes for the N-terminal methionine of cGH. SW272/cGH is designed to express cGH mRNA transcripts from the viral promoter.

Figure 2:
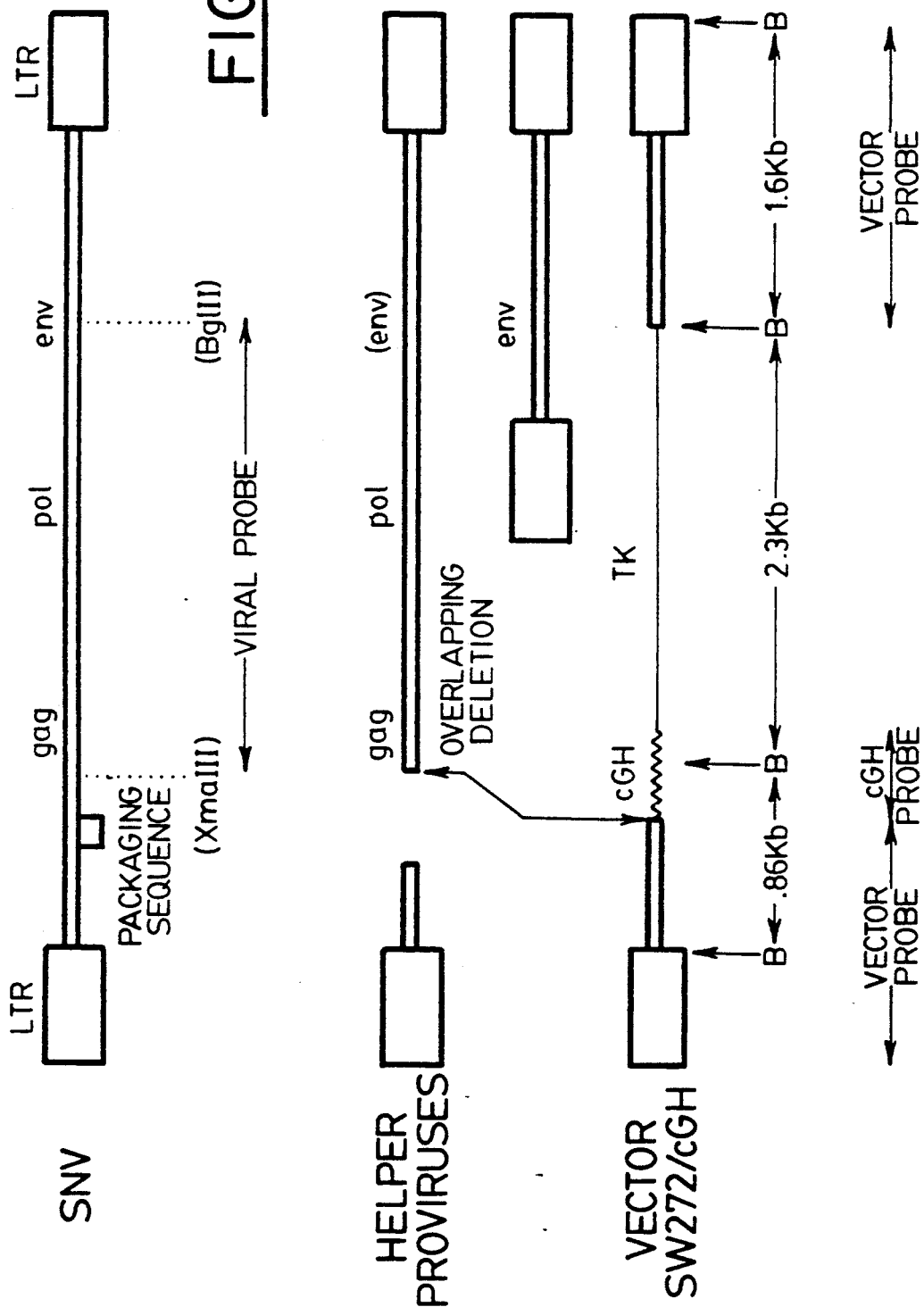
FIG. 2 depicts in schematic form the sequence relationships between SNV, pSW272/cGH and the packaging defective helper proviruses present in the C3 helper cell line.

The sequence relationships between SNV, SW272/cGH and the packaging defective helper proviruses present in the C3 helper cell line are shown in FIG. 2. Relevant features of these proviruses include the long terminal repeats (LTR's), the structural genes of the virus (gag, pol, env), the approximate position of the packaging sequence, the cGH sequences, and the HSV-I tk sequences. The env sequence in the larger of the two helper proviruses is presumably not expressed due to the removal of the 5' splice donor. Overlapping deletions indicated between helper and vector sequences act to reduce recombination between these genomes. Further details of this system and a complete description of the synthesis of the replication-defective retroviral vector (pSW272), the selection of the host cell (D17), the synthesis of two complementary helper gene sequences in plasmid vectors (pSW279 and pSW283) and the construction of the C3 helper cell line containing packaging defective helper proviruses are found in U.S Pat. No. 4,650,764. Relative size of the BamHI (B) restriction endonuclease fragments with vector pSW272/cGH are indicated in FIG. 2 as 0.86 kb, 2.3 kb and 1.6 kb. FIG. 2 also shows the location of the viral vector and cGH specific DNA probes used to analyze the genetic sequences transferred by transfection according to this Example 1 or transferred by microinjection as described in Example 2.

Careful screening of the C3 helper cells transfected with vectors pSW272/cGH and pHyg yielded clone C3-44 which released $2 \times 10^4$ TKTU/ml into growth media, but very low levels of competent virus. Hu, et al., Virology 159:446-449 (1987). Transfection was accomplished according to the method of Graham and Van der Eb, J. Virology 52:456-467 (1973). Transfected cells were selected for 10 to 14 days in media containing 200 μg/ml hygromycin. Sudgen, et al., Mol. Cell. Biol. 5:410-413 (1985). Western blot analysis (Burnette, Anal. Biochem. 112: 195-203 (1981)) of cGH released by pSW272/cGH transfected C3-44 cells was performed. Medium from cultures of C3-44 was subjected to electrophoresis under reducing conditions in 15% polyacrylamide. Antiserum from a rabbit immunized with recombinant cGH was used for immunodetection. The cGH released by the C3-44 cells was readily detectable as a predominantly single band of protein which comigrated with purified recombinant cGH. The migration of purified recombinant cGH at various concentrations (100, 50, 25 and 10 ng) was compared with the migration of cGH from conditioned media of C3-44 cells, which are the C3 cells transfected with pSW272/cGH. Control samples were conditioned medium from uninfected D17 cells and culture medium alone. The observed molecular weight of cGH was about 23,000 daltons. The estimated concentration of cGH in medium of clone C3-44 was at least 500 ng/ml. Chicken embryo fibroblasts (Vogt, P.K., *Fundamental Techniques in Virology*, Academic Press, N.Y. (1969) at pp. 198-211) infected with vector according to the method of Watanabe and Temin, Proc. Natl. Acad. Sci. USA 79:5986-5990 (1982) released greater than 40 ng cGH per ml of growth media as determined by radioimmunoassay (Souza, et al., supra) three days after infection. Western blot analysis of cGH released by D17 and QT-6 cell lines infected with the SW272/cGH vector was performed for clones B56, B20, QT82, QT54, QT15, and QT8. Cell lines B56 and B20 derive from D17 cells. Cell lines QT82, QT54, QT15, and QT8 derive from QT-6 cells. All of these cells release cGH having the same apparent molecular weight as purified recombinant cGH (23,000 datons). Souze, et al., supra. Approximate levels of cGH expresion varied from 2 to 10 ng/ml.

For the above described experimetns, various cell lines were obtained and grown as follows. The REV-A helper cell line, C3, as described by Watanabe and Temin, Proc. Natl. Acad. Sci. USA 79:5986-5990 (1982) was obtained from H. Temin. C3 cells were cultured in Eagle's minimal essential medium (MEM) containing 7% fetal calf serum (FCS), and 400 $\mu$g/ml G418. Watanabe and Temin, supra. Chicken embryo fibroblasts were grown in F-10 medium supplemented with 10% tryptose phosphate broth, 5% calf serum. Vogt, P.K., supra. D17 cells were cultured in MEM, 7% FCS, as described by Watanabe and Temin, supra. Buffalo rat liver thymidine kinase negative (BRLtk$^-$) cells were grown in MEM plus 7% calf serum as described by Watanabe and Temin, supra. QT-6 cells were obtained from C. Moscovici, and grown as described by Moscovici et al., Cell 11:95-103 (1977).

EXAMPLE 2

Gene Transfer into Chicken Embryos

Five to 20 $\mu$l volumes of tissue culture fluid containing the vector SW272/cGH were injected beneath and around the blastoderms of unincubated or briefly incubated chicken embryos. The method of injection was as follows. Unincubated chicken eggs either newly laid, one day or 2 day old, or alternatively chicken eggs that had been briefly incubated ($\sim$45 minutes at 37° C.), were windowed in order to expose very young embryos as follows. The eggs were held horizontally with respect to their long axis for 5 hours or more at 18° to 20° C. During this period, the blastoderm positions itself just beneath the topmost area of the shell. Egg surfaces were wiped with 70% ethanol before and after a 5-8 mm circular hole was made in the shell. This was accomplished by drilling an opening, normally by the use of a drilling tool fitted with an abrasive rotating tip which can drill a hole in the eggshell without damaging the underlying shell membrane. A Dremel (Model 280-5) moto-tool fitted with an aluminum oxide grinding stone (Dremel, #924) is suitable. The membrane beneath the hole in the shell in the area above the blastoderm is then cut out by use of a scalpel. Small volumes (generally 5-20 $\mu$l, however, smaller or larger volumes may be used) of a solution containing the vector were administered through the opening by microinjecting directly beneath the exposed blastoderm using a Narishigi micromanipulator and a 25 $\mu$l Drummond pipette fitted with a glass needle 40-60 $\mu$M in outer diameter. The vector solution for microinjection typically contained about $10^4$ infectious units (IU)/ml and was prepared from media harvested from cultures of C3 cells which contain the vector as follows. C3 cells containing the vector SW272/cGH were cultured in MEM containing 5-7% FCS at 37° C. overnight. The cultures after this incubation were $\sim$80% confluent. The culture media from the overnight culture were removed and centrifuged in a microfuge for 3 minutes. These supernatant fluids were used for microinjection. One infectious unit of vector is defined as one infectious viral particle which transduces the TK gene present in the vector into one BRL tk$^-$ cell.

After microinjection, eggs were resealed with donor shell membrane (from another egg of similar age) and with paraffin, glue or Duco cement (Devcon ®). The resealed eggs were then incubated at 37° C. to permit continued growth and development. Total embryonic DNA was isolated after seven days of development according to the method of DNA isolation as described in Maniatis et al., *Molecular Cloning: A Laboratory Manual*, Cold Spring Harbor Laboratory, N.Y. (1982) at pp. 280-281, and analyzed by dot blot hybridization. Dot blot hybridization was carried out as follows. DNA samples were applied to Gene Screen Plus membranes (New England Nuclear Co.) by means of 96-well plexiglass manifolds. DNA on membranes was denatured in 1.5M NaCl and 0.5M NaOH for 15 minutes, neutralized in 0.5M Tris pH 7.5 and 1.5 M NaCl for 1 minute, blotted dry, and baked at 80° C. for 30 minutes. Hybridizations were carried out as described by Hu et al., Virology 159: 446-449 (1987). Radiolabeled DNA probe was prepared by the method of random priming. Feinberg and Vogelstein, Anal. Biochem. 132: 6-13 (1983). DNA from 18 out of 25 injected embryos hybridized to a radiolabeled probe of vector DNA. The vector probe used is illustrated in FIG. 2.

To confirm the presence and correct genome organization of vector sequences in infected 7 day embryos, high molecular weight DNA's from several vector containing embryos (designated as embryos 1, 2, 6, 7, and 8) were digested with BamHI endonuclease and subjected to Southern blot analysis. Southern, J. Mol Biol. 98:503-517 (1975). The following fragments were analyzed: DNA fragments of HindIII digested lambda phage DNA; HaeIII digested $\phi$X174 DNA; BamHI digested uninjected chicken blood DNA; BamHI digested DNA from uninjected embryos; BamHI digested DNA from uninjected chicken blood; BamHI digested DNA from vector injected embryos 1, 2, 6, 7, and 8; and BamHI digested DNA of pSW272/cGH plus uninjected chicken blood DNA. BamHI fragments internal to the proviral vector and BamHI fragments containing the endogenous cGH sequence could be identified. The same filter was hybridized to three different probes: (1) hybridization was with the pSW272 specific probe (parental vector which does not contain cGH sequence); (2) hybridization was with the cGH specific probe; and (3) hybridization was with the virus specific probe. Sequences recognized by these probes are illustrated in FIG. 2.

Using first the pSW272 specific probe, DNA's from 5 of the vector infected 7 day embryos showed the expected BamHI vector DNA fragments of 0.86 kb 1.6 kb and 2.2 kb illustrated in FIG. 2. The absence of detectable BamHI fragments containing the junction of cellular DNA and integrated vector DNA indicated multiple sites of proviral integration during infection of early embryonic cells. No 0.57 kb BamHI fragment predicted from the structure of unintegrated circular forms of the vector DNA was observed. No 1.38 kb fragment diagnostic of the 5' end of integrated REV proviral DNA was observed. Watanabe and Temin, Mol. Cell. Biol. 3:2241-2249 (1983). BamHI digested control DNA from uninjected whole embryos or from blood of uninjected chickens did not hybridize to the vector probe.

Following removal of the SW272 vector probe, the same filter was hybridized with a cGH specific probe. Using the cGH specific probe, two fragments of 0.86 kb and 2.3 kb can be detected, which are the predicted cGH containing vector sequences described in FIG. 2. In addition, two bands can be detected which represent BamHI fragments of ~5.5 kb and ~2.7 kb that are derived from the endogenous cGH gene. As expected, the DNA of each embryo tested contained all four fragments derived from both the vector and endogenous cGH gene that hybridized with the cGH specific probe. The 1.6 kb BamHI fragment detected as described above with the pSW272 specific probe, does not hybridize with the cGH specific probe.

Removal of the vector and cGH probes from the filter and subsequent hybridization with virus specific probe did not detect the presence of replicating helper virus. The parental SNV and REV-A proviruses used to derive the helper cell and vectors described herein contain internal BamHI fragments of 1.3 kb, 1.6 kb, 2.3 kb, 0.7 kb and 1.6 kb. Only the 1.6 kb fragment would not be detected by the virus specific probe. No virus specific BamHI fragments were observed, indicating that endogenous and exogenous REV sequences were not detectable. These results show that genetic sequences are transduced by the replication-defective REV vector into embryonic chicken cells in the absence of a replication competent helper virus (i.e. no exogenous virus) and that prior insertion of REV sequences has not occurred in nature in these embryos (i.e. no endogenous virus).

DNA from brain, liver, and muscle of four fourteen-day embryos infected prior to incubation was analyzed by dot blot hybridization. Two of the four embryos contained vector specific sequences in all three tissues. One embryo contained vector sequences in liver and muscle only. The fourth embryo was negative in brain and muscle. Similar analysis of RNA from brain, liver, and muscle of infected 15-day embryos showed the presence of vector specific RNA transcripts in all three tissues.

Chicken growth hormone expression was analyzed either by radioimmunoassay (RIA). as described by Souza, et al., J. Exp. Zool. 232:465-473 (1984), or by Western blotting as described by Burnette, Anal. Biochem. 112: 195-203 (1981). Circulating levels of cGH were determined by RIA of serum from thirty 15-day old embryos infected with vector prior to incubation and are shown in Table 1. Concentrations of cGH in serum from seventeen of the thirty injected embryos ranged from 10 to 254 ng/ml. All thirty-five control embryos contained less than 2 ng/ml of detectable serum cGH.

TABLE I

| cGH Levels in Chicken Embryo Sera[a] | |
|---|---|
| Bird # | |
| SW272/cGH Injected Embryos | |
| 1 | 51.0 |
| 2 | 180.0 |
| 3 | 100.0 |
| 4 | 0.9 |
| 5 | 41.0 |
| 6 | 200.0 |
| 7 | 2.6 |
| 8 | 80.0 |
| 9 | 44.0 |
| 10 | 106.0 |
| 11 | 4.5 |
| 12 | 18.0 |
| 13 | 8.6 |
| 14 | 1.1 |
| 15 | 0.92 |
| 16 | 2.2 |
| 17 | 0.8 |
| 18 | 254.0 |
| 19 | 10.8 |
| 20 | 240.0 |
| 21 | 168.0 |
| 22 | 32.0 |
| 23 | 56.0 |
| 24 | 12.0 |
| 25 | 42.0 |
| 26 | 0.86 |
| 27 | 0.70 |
| 28 | 3.4 |
| 29 | 1.4 |
| 30 | 0.76 |
| Uninjected Embryos | |
| 31 | <0.80 |
| 32 | <0.80 |
| 33 | <0.80 |
| 34 | <0.80 |
| 35 | <0.80 |
| 36 | 0.85 |
| 37 | <0.80 |
| 38 | <0.80 |
| 39 | <0.80 |
| 40 | <0.80 |
| 41 | <0.80 |
| 42 | 1.2 |
| 43 | 1.0 |
| 44 | <0.8 |
| 45 | <0.8 |
| 46 | <0.8 |
| 47 | <0.8 |
| 48 | <0.8 |
| 49 | 1.1 |
| 50 | 1.2 |
| 51 | 1.2 |
| 52 | 0.9 |
| 53 | 1.2 |
| 54 | 0.9 |
| 55 | <0.8 |
| 56 | <0.8 |
| 57 | <1.1 |
| 58 | <0.8 |
| 59 | <0.8 |
| 60 | <0.8 |
| 61 | <0.8 |
| 62 | <0.8 |
| 63 | <0.8 |
| 64 | <0.8 |
| 65 | <0.8 |

[a]Embryos of unincubated eggs were injected with 10 μl of media from cultures of C3-44. After 15 days of incubation serum from each embryo was assayed by RIA for cGH, expressed here in ng/ml of serum.

Analysis of hatched chickens (Example 3) supports the results obtained with embryos discussed above. The data from gene transfer into embryos as described show that REV based vectors can be used to introduce new genes into pluripotent stem cells. The stem cells can then differentiate into somatic and germ cells of the chicken resulting in the production of transgenic chickens. However, not all the embryos injected with a replication-defective REV vector are viable and hatch.

The percent viability appears to vary depending on the vector injected. For example, approximately 8.5% (182/2166) of the chicken embryos injected with the vector SW272/cGH as described above were viable, and hatched following a normal incubation period. In contrast, approximately 38% (995/2599) of the chicken embryos injected with the ME111 vector hatched.

EXAMPLE 3

Analysis of Hatched Chickens

Chicken embryos injected with vector SW272/cGH as described in Example 2 were allowed to hatch by incubating the sealed eggs at 37° C. Blood cell DNA from all hatched chickens (male and female) was analyzed for the presence of vector DNA. Birds containing vector DNA in their blood were further tested for the presence of replicating virus by cocultivating virus free chicken embryo fibroblasts with blood from vector positive birds as described by Hu et al., Virology 159:446-449 (1987). Virus negative, vector positive birds were grown to maturity. In addition, all male birds with or without vector sequences in their blood DNA were grown to maturity, and subsequently tested by nucleic acid hybridization and Southern blotting for the presence of vector DNA in their semen. At least three male birds of 285 infected embryonically with SW272/cGH hatched and contained vector sequences in semen DNA. Nucleic acid hybridization data indicated that about 1-2% of sperm cells from these birds contained vector sequences. Comparable results have been achieved with a similar vector, ME111, as described in Example 4 below, which contains a neomycin phosphotransferase coding sequence in place of the cGH sequence. Thirty-three of approximately 380 males similarly examined did contain vector sequences in their semen DNA. The presence of vector sequences in the DNA isolated from semen strongly indicates that an REV derived a replication-defective vector such as SW272/cGH can be used to insert new genetic information into pluripotent chicken embryonic stem cells which eventually develop into germ cells.

EXAMPLE 4

Analysis of Transgenic Chickens

Figure 3:
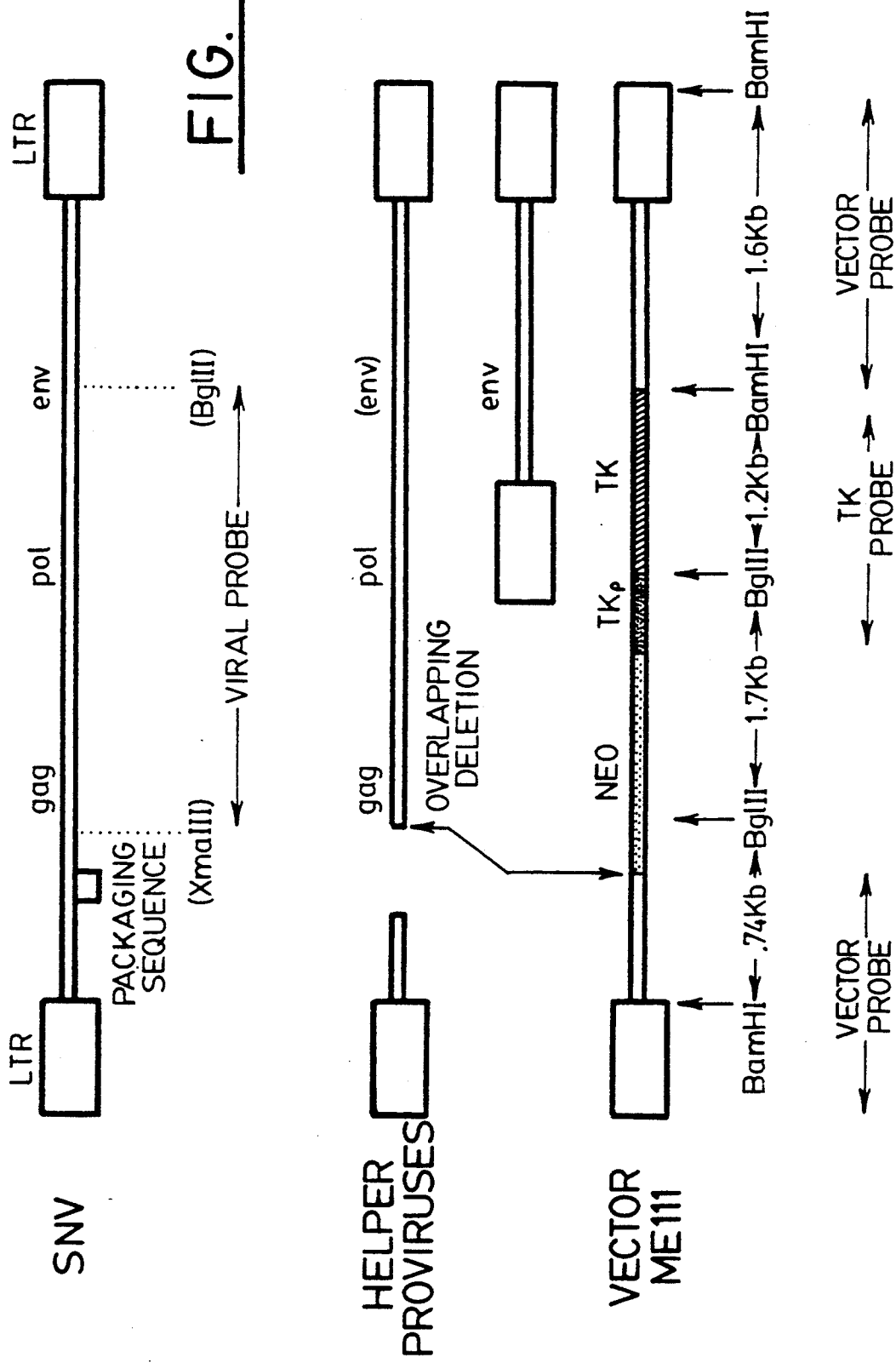
FIG. 3 depicts in schematic form the sequence relationships between SNV, ME111 and the modified packaging defective helper proviruses.

Vector positive $G_0$ male chickens were produced by injecting unincubated embryos with the replication-defective REV vectors SW272/cGH or ME111, and used in breeding studies to demonstrate heritable, germline transfer of vector sequences to $G_1$ progeny Injection of the ME111 vector was accomplished as described in Example 2 for injection of the SW272/cGH vector. The ME111 vector lacks all viral structural genes and carries both the Tn5 neomycin resistance gene driven by the promoter of the REV LTR and the HSV-I tk gene Emerman and Temin, Cell 39:459-467 (1984). The sequence relationships between SNV, the modified packaging defective helper proviruses, and the ME111 proviral vector are shown in FIG. 3. Relevant features of these proviruses shown in FIG. 3 include the LTR's, the structural genes of the virus (gag, pol, env), the approximate position of the packaging sequence, the neomycin phosphotransferase sequences (neo), and the HSV-I tk gene (TK). TKp indicates the TK promoter. The env sequence in the larger of the two helper proviruses is presumably not expressed due to removal of the 5' splice donor. Overlapping deletions indicated between helper and vector sequences act to reduce recombination between these genomes. Further details and a description of the REV helper proviruses and the ME111 vector are found in Emerman and Temin, supra, and Watanabe and Temin, Proc. Natl. Acad. Sci. USA 79:5986-5990 (1982). The 5' LTR's of both helper proviruses are derived from SNV and their coding sequences from REV-A. REV-A and SNV share high sequence homology. FIG. 3 shows the BamHI and BglII restriction endonuclease fragments, although not drawn to scale. FIG. 3 also shows the location of the viral, vector and TK specific DNA probes used to analyze transferred genetic sequences.

Semen was collected from SW272/cGH and ME111 vector positive male birds, and used to inseminate uninjected control female chickens. Blood DNA from progeny chickens ($G_1$) was assayed by nucleic acid hybridization using a probe which specifically hybridized to vector DNA. Five of 569 $G_1$ progeny from a single $G_0$ SW272/cGH positive male contained vector sequences in their blood DNA. Southern blot analysis of BamHI digested blood DNA from these birds showed fragments of 0.86 kb, 2.2 kb, and 1.6 kb when hybridized with vector specific DNA probes (see FIG. 2 for the predicted BamHI fragments and the vector specific probe used for analysis). The presence of an additional fourth hybridizing fragment observed in DNA from each $G_1$ bird represents a junction fragment between vector and cellular sequences adjacent to the 5' side of the site in cellular DNA into which vector DNA was integrated following original infection of $G_0$ embryos.

These results confirm heritable, germline passage of REV vector SW272/cGH sequences from embryonically infected $G_0$ chickens to their $G_1$ progeny. Similar results were achieved with the vector ME111. Blood DNAs from 760 of the hatched chicks injected with ME111 were analyzed by hybridization with a vector specific probe. One hundred seventy-three of these $G_0$ chicks contained vector sequences in their blood DNA. Southern blot analysis of BamHI digested DNA from these $G_0$ chicks using a vector specific probe derived for the 5' and 3' ends of the ME111 vector (as shown in FIG. 3) showed the predicted internal BamHI DNA fragments of 3.7 kb and 1.65 kb which derive from within the provirus. Additional DNA fragments were observed that appeared to represent fragments derived from the 5' junction between cellular and proviral DNAs. These results suggest that multiple blood cell precursors were infected when the embryo was originally injected with ME111 vector. When a virus specific probe was used for hybridization no replication competent virus was detected, as would have been indicated by the presence of a 1.3 kb virus specific BamHI fragment. Thus, just as with SW272/cGH vector as described in Example 2, no endogenous or exogenous REV sequences were detectable.

Thirty-three of 82 $G_0$ males that carried ME111 vector sequences in their blood also carried ME111 vector sequences in their semen. Vector positive semen from 4 $G_0$ males was used to inseminate control females. Each of the $G_0$ males did transmit vector sequences to their $G_1$ progeny at frequencies which varied between 2% and 8% as follows: 3.8% (11/289) of Male 1 progeny; 4.4% (9/205) of Male 2 progeny; 8.4% (12/143) of Male 3 progeny; and 2.4% (2/83) of Male 4 progeny. When the BamHI digested DNA from the $G_1$ progeny of these four ME111 injected $G_0$ males were similarly tested by Southern blot analysis using the vector specific probe, the expected internal BamHI DNA fragments of 3.7 kb and 1.65 kb were observed. Additional DNA fragments were observed that may represent the 5' junctions between cellular DNA and integrated proviral DNA. Southern blot analysis of BamHI and BglII digested DNA from these $G_1$ progeny using both a vector specific probe and a TK specific probe suggested that some sequences were deleted between the two BglII sites of the ME111 vector.

Further analysis of three $G_1$ progeny of one $G_0$ male showed that the insertion sites of ME111 provirus were different in each of the three $G_1$ progeny and in one of the three, two copies of inserted proviral vectors were detected. Thus, the gonads of the $G_0$ males appear to be mosaic with respect to vector insertions. The progeny of such mosaics could therefore carry proviral insertions at many different points within the genome.

In summary, the results just discussed demonstrate successful germline transfer of vector sequences. Of 5 $G_0$ males that were bred (4 had been injected as embryos with the ME111 vector and 1 had been injected as an embryo with SW272/cGH vector), all 5 passed vector sequences on to a fraction of their offspring ($G_1$). The percentage of these $G_1$ (transgenic) offspring with vector sequences varied between 1% and approximately 8%

It will therefore be appreciated that the present invention provides a method for infecting avian embryo cells with any prokaryotic or eukaryotic gene of interest using a replication-defective retroviral vector. The retrovirus can be grown to a stock of any desired size, yet when removed from the helper cell (for example, C3 cells for the pSW272/cGH vector), it will not replicate further.

As discussed above, it is expected that many types of prokaryotic genes other than the neomycin resistance gene and many types of eukaryotic genes other than the thymidine kinase gene or the chicken growth hormone gene will be appropriate for transfer with a retroviral vector. Any gene identified as one useful for poultry improvement will be particularly suitable for transfer. Moreover, it is expected that other types of retroviral vectors besides pSW272, pSW272/cGH or ME111 will prove suitable as vectors. As such, the invention should not be limited by the illustrative embodiments described above. Instead, the invention is to be judged by the claims which follow.

what is claimed is:

1. A method for transferring a nucleic acid sequence of a replication-defective REV-derived vector into germ cells of a chicken in the absence of an exogenous replication-competent helper retrovirus comprising introducing the nucleic acid sequence into pluripotent stem cells of an embryo of a chicken at a stage in development wherein the stem cells are capable of being infected by the vector and providing the vector in an amount effective to transfer the nucleic acid sequence into the stem cells.

2. A method according to claim 1 wherein the replication-defective REV-derived vector comprises a non-retroviral derived nucleic acid sequence.

3. A method according to claim 2 wherein the non-retroviral derived nucleic acid sequence is a thymidine kinase gene.

4. A method according to claim 2 wherein the non-retroviral derived nucleic acid sequence is a neomycin resistance gene.

5. A method according to claim 2 wherein the non-retroviral derived nucleic acid sequence is a chicken growth hormone gene.

6. A method for introducing a replication-defective REV-derived vector in the absence of an exogenous replication-competent helper retrovirus into a pluripotent stem cell of chicken embryo comprising:
    (a) making an opening in a laid chicken egg which is not more than two days old and which contains the embryo to expose a blastoderm;
    (b) microinjecting through the opening a solution containing the replication-defective REV-derived vector into an area around and in close proximity to the blastoderm; and
    (c) sealing the opening after microinjection.

7. A method according to claim 6 wherein the replication-defective REV-derived vector comprises a non-retroviral derived nucleic acid sequence.

8. A method according to claim 7 wherein the non-retroviral derived nucleic acid sequence is a thymidine kinase gene.

9. A method according to claim 7 wherein the non-retroviral derived nucleic acid sequence is a neomycin resistance gene.

10. A method according to claim 7 wherein the non-retroviral derived nucleic acid sequence is a chicken growth hormone gene.

11. A method for obtaining a transgenic chicken whose germ cells contain a nucleic acid sequence of a replication-defective REV-derived vector in the absence of an exogenous replication-competent helper retrovirus comprising:
    (a) obtaining a laid chicken egg which is not more than two days old and which contains an embryo;
    (b) making an opening in the egg to expose a blastoderm;
    (c) microinjecting through the opening a solution containing the replication-defective REV-derived vector into an area around and in close proximity to the blastoderm;
    (d) sealing the opening after microinjection;
    (e) incubating the sealed microinjected egg at 37° C. to allow development of the embryo;
    (f) maintaining the incubation until the chicken is viably hatched from the egg;
    (g) breeding said chicken to produce progeny chickens; and
    (h) identifying progeny chickens not productively infected by the helper retrovirus and carrying the nucleic acid sequence.

12. A method according to claim 11 wherein the replication-defective REV-derived vector comprises a non-retroviral derived nucleic acid sequence.

* * * * *